US010548321B2

(12) United States Patent
Gewehr et al.

(10) Patent No.: US 10,548,321 B2
(45) Date of Patent: Feb. 4, 2020

(54) PESTICIDAL MIXTURES

(71) Applicant: BASF SE, Ludwigshsafen (DE)

(72) Inventors: Markus Gewehr, Kastellaun (DE); Egon Haden, Ludwigshafen (DE); Lutz Brahm, Worms (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/561,443

(22) Filed: Dec. 5, 2014

(65) Prior Publication Data

US 2015/0087511 A1 Mar. 26, 2015

Related U.S. Application Data

(62) Division of application No. 13/498,766, filed as application No. PCT/EP2010/064093 on Sep. 24, 2010.

(30) Foreign Application Priority Data

Sep. 29, 2009 (EP) .................................... 09171634
Sep. 29, 2009 (EP) .................................... 09171645

(51) Int. Cl.
*A01N 47/24* (2006.01)
*A01N 53/00* (2006.01)
*A01N 43/88* (2006.01)
*A01N 43/54* (2006.01)

(52) U.S. Cl.
CPC ............ *A01N 53/00* (2013.01); *A01N 43/54* (2013.01); *A01N 43/88* (2013.01); *A01N 47/24* (2013.01)

(58) Field of Classification Search
None
See application file for complete search history.

(56) References Cited

U.S. PATENT DOCUMENTS

| 2005/0009703 A1 | 1/2005 | Wachendorff-Neumann et al. |
| 2008/0070785 A1 | 3/2008 | Walter et al. |
| 2008/0274882 A1 | 11/2008 | Krohn et al. |
| 2009/0247511 A1 | 10/2009 | Suty-Heinze et al. |

FOREIGN PATENT DOCUMENTS

| CA | 2324460 | 9/1999 |
| DE | 102004062513 | 7/2006 |
| EP | 0 213 718 | 6/1991 |
| JP | 2000 336008 | 12/2000 |
| JP | 2002 003310 | 1/2002 |
| WO | WO 99/48366 | 9/1999 |
| WO | WO 03/015515 | 2/2003 |
| WO | WO 2005/102057 | 11/2005 |
| WO | WO 2006/023899 | 3/2006 |
| WO | WO 2006/089876 | 8/2006 |
| WO | WO 2007/147548 | 12/2007 |
| WO | WO 2008/000377 | 1/2008 |
| WO | WO 2008/095913 | 8/2008 |
| WO | WO 2009/003953 | 1/2009 |
| WO | WO 2010/003877 | 1/2010 |
| WO | WO 2011/039105 | 4/2011 |
| WO | WO 2011/067205 | 6/2011 |
| WO | WO 2011/067209 | 6/2011 |
| WO | WO 2011/069967 | 6/2011 |

OTHER PUBLICATIONS

Office Action, issued in U.S. Appl. No. 15/211,725, dated Apr. 4, 2017.
Office Action, issued in U.S. Appl. No. 13/498,766, dated Dec. 20, 2016.
Office Action, issued in U.S. Appl. No. 15/211,738, dated Apr. 4, 2017.
Anonymous, "Mixtures of fungicides and insecticides", Research Disclosure, Mason Publications, Hampshire GB, Jun. 1, 1992, vol. 338, No. 93.
Tomlin, C.D.C, "840 Triazamate", the E-Pesticide Manual: A world Compendium, Alton : British Crop Protection Council, Jul. 1, 2006, pp. 1-2, vol. 4.0.
International Search Report completed Aug. 30, 2008, in International Application No. PCT/EP2010/064093, filed Sep. 24, 2010.
English language translation of the International Preliminary Report on Patentability dated Apr. 3, 2012, from corresponding International Application No. PCT/EP2010/064093, filed Sep. 24, 2010.
Clement et al., "Field Tests with Two New Insect Growth Regulators for the Control of Diamondback Moth *Plutella xylostella* L.", Indian Journal of Plant Protection (1991), vol. 19, Issue 2, pp. 161-166.
Office Action for U.S. Appl. No. 13/513,323, dated Apr. 16, 2013.
Office Action for U.S. Appl. No. 13/513,323, dated Dec. 3, 2013.
Office Action for U.S. Appl. No. 13/513,323, dated Dec. 18, 2014.
Office Action for U.S. Appl. No. 13/498,203, dated Oct. 17, 2013.
Office Action for U.S. Appl. No. 13/498,203, dated Jan. 31, 2013.
Final Office Action, issued in co-pending U.S. Appl. No. 13/498,766, dated Oct. 4, 2017.

(Continued)

*Primary Examiner* — Melenie L Gordon
*Assistant Examiner* — Andrew P Lee
(74) *Attorney, Agent, or Firm* — Brinks Gilson & Lione

(57) ABSTRACT

The present invention relates to synergistic mixtures comprising, as active components one insecticidal compound I selected from the group of acrinathrin, allethrin, alpha-cypermethrin, beta-cypermethrin, bifenthrin, cycloprothrin, cyfluthrin, cypermethrin, cyphenothrin, deltamethrin, dimefluthrin, esfenvalerate, etofenprox, fenpropathrin, fenvalerate, flucythrinate, imiprothrin, permethrin, prallethrin, profluthrin, pyrethrin I, pyrethrin II, resmethrin, silafluofen, tau-fluvalinate, tetramethrin, theta-cypermethrin, tralomethrin, transfluthrin and zeta-cypermethrin; and one fungicidal compound II selected from the group of azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxysstrobin, 2-(ortho -((2,5-Dimethylphenyl-oxymethylen)phenyl)-3-methoxy-acrylic acid methyl ester, 2-(2 -(3-(2,6-dichlorophenyl)-1-methyl-allylideneaminooxymethyl)-phenyl)-2-methoxyimino -N-methyl-acetamide in synergistic effective amounts.

7 Claims, No Drawings

(56) References Cited

OTHER PUBLICATIONS

Final Office Action, issued in co-pending U.S. Appl. No. 15/211,738, dated Oct. 17, 2017.
Final Office Action, issued in co-pending U.S. Appl. No. 15/211,725, dated Oct. 17, 2017.
Thompson, "Assessment of the Synergy and Repellency of Pyrethroid/Fungicide Mixtures," Bulletin of Insectology, vol. 56, No. 1, (2003), pp. 131-134.
Office Action, issued in co-pending U.S. Appl. No. 15/211,738, dated May 15, 2018.
Office Action, issued in co-pending U.S. Appl. No. 15/211,725, dated May 23, 2018.
Office Action, issued in co-pending U.S. Appl. No. 13/498,766, dated Jun. 21, 2018.

PESTICIDAL MIXTURES

This application is a divisional application of U.S. patent application Ser. No. 13/498,766, filed Mar. 28, 2012, the entire contents of which is hereby incorporated herein by reference. U.S. patent application Ser. No. 13/498,766 is a National Stage application of International Application No. PCT/EP2010/064093, filed Sep. 24, 2010, the entire contents of which is hereby incorporated herein by reference. This application also claims priority under 35 U.S.C. § 119 to European Patent Application Nos. 09171645.6 and 09171634.0, both filed on Sep. 29, 2009, the entire contents of which are hereby incorporated herein by reference.

The present invention relates to synergistic mixtures comprising, as active components
1) one insecticidal compound I selected from the group of acrinathrin, allethrin, alpha-cypermethrin, beta-cypermethrin, bifenthrin, cycloprothrin, cyfluthrin, cypermethrin, cyphenothrin, deltamethrin, dimefluthrin, esfenvalerate, etofenprox, fenpropathrin, fenvalerate, flucythrinate, imiprothrin, permethrin, prallethrin, profluthrin, pyrethrin I, pyrethrin II, resmethrin, silafluofen, tau-fluvalinate, tetramethrin, theta-cypermethrin, tralomethrin, transfluthrin and zeta-cypermethrin; and
2) one fungicidal compound II selected from the group of azoxystrobin, coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-(ortho-((2,5-Dimethylphenyl-oxymethylen)phenyl)-3-methoxy-acrylic acid methyl ester, 2-(2-(3-(2,6-dichlorophenyl)-1-methyl-allylideneaminooxymethyl)-phenyl)-2-methoxyimino-N-methyl-acetamide;
in synergistic effective amounts.

These above-referred mixtures are hereinbelow also referred as "inventive mixtures".

Moreover, the invention relates to a method for controlling phytopathogenic pests, this refers to includes phytopathogenic animal pests and phytopathogenic harmful fungi, using the inventive mixtures and to the use of compound I and compound II for preparing such mixtures, and also to compositions comprising such mixtures.

In one embodiment, the present invention provides methods for the control of phytopathogenic animal pests (such as insects, acarids or nematodes) comprising contacting the animal pest (the insect, acarid or nematode) or their food supply, habitat, breeding grounds or their locus with a pesticidally effective amount of the inventive mixtures.

Moreover, in another embodiment the present invention also relates to a method of protecting plants from attack or infestation by phytopathogenic animal pests (insects, acarids or nematodes) comprising contacting the plant, or the soil or water in which the plant is growing, with a pesticidally effective amount of the inventive mixture.

Moreover, the invention relates to a method for controlling phytopathogenic harmful fungi comprising contacting the phytopathogenic harmful fungi, their habitat, breeding grounds, their locus or the plants to be protected against fungal attack, the soil or plant propagation material with an effective amount of a mixture as defined above.

Additionally, the present invention also comprises a method for protection of plant propagation material from phytopathogenic pests, such as phytopathogenic animal pests (insects, arachnids or nematodes) and phytopathogenic harmful fungi comprising contacting the plant propagation materials with an inventive mixture in pesticidally effective amounts The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. These young plants may also be protected before transplantation by a total or partial treatment by immersion or pouring. In a particular preferred embodiment, the term propagation material denotes seeds.

The present invention further relates to plant-protecting active ingredient mixtures having synergistically enhanced action of improving the health of plants and to a method of applying such inventive mixtures to the plants.

WO 07/147,548 discloses specific ternary mixtures of azoxystrobin with tebuconazole that may comprise a further insecticidal compound (lamda-cyhalothrin or tefluthrin are mentioned therein).

However, the specific mixtures of the present invention are not mentioned therein.

The compounds I and II as well as their pesticidal action and methods for producing them are generally known. For instance, the commercially available compounds may be found in The Pesticide Manual, 14th Edition, British Crop Protection Council (2006) among other publications.

One typical problem arising in the field of pest control lies in the need to reduce the dosage rates of the active ingredient in order to reduce or avoid unfavorable environmental or toxicological effects whilst still allowing effective pest control.

In regard to the instant invention the term "phytopathogenic pests" embrace phytopathogenic animal pests, and phytopathogenic harmful fungi. The term phytopathogenic animal pests is hereinbelow abbreviated as "animal pest" and the term phytopathogenic harmful fungi is hereinbelow abbreviated as "harmful fungi".

Another problem encountered concerns the need to have available pest control agents which are effective against a broad spectrum of pests, e.g. both animal pests and harmful fungi.

There also exists the need for pest control agents that combine knock-down activity with prolonged control, that is, fast action with long lasting action.

Another difficulty in relation to the use of pesticides is that the repeated and exclusive application of an individual pesticidal compound leads in many cases to a rapid selection of pests, that means animal pests, and harmful fungi, which have developed natural or adapted resistance against the active compound in question. Therefore there is a need for pest control agents that help prevent or overcome resistance.

Another problem underlying the present invention is the desire for compositions that improve plants, a process which is commonly and hereinafter referred to as "plant health".

The term plant health comprises various sorts of improvements of plants that are not connected to the control of pests. For example, advantageous properties that may be mentioned are improved crop characteristics including: emergence, crop yields, protein content, oil content, starch content, more developed root system (improved root growth), improved stress tolerance (e.g. against drought, heat, salt, UV, water, cold), reduced ethylene (reduced production and/or inhibition of reception), tillering increase, increase in plant height, bigger leaf blade, less dead basal leaves, stronger tillers, greener leaf color, pigment content, photosynthetic activity, less input needed (such as fertilizers or water), less seeds needed, more productive tillers, earlier flowering, early grain maturity, less plant verse (lodging), increased shoot growth, enhanced plant vigor, increased plant stand and early and better germination; or any other advantages familiar to a person skilled in the art.

It was therefore an object of the present invention to provide pesticidal mixtures which solve the problems of reducing the dosage rate and/or enhancing the spectrum of activity and/or combining knock-down activity with prolonged control and/or to resistance management and/or promoting the health of plants.

We have found that this object is in part or in whole achieved by the complex mixtures comprising the active compounds defined in the outset.

Especially, it has been found that the mixtures as defined in the outset show markedly enhanced action against pests compared to the control rates that are possible with the individual compounds and/or is suitable for improving the health of plants when applied to plants, parts of plants, plant propagation materials (preferably seeds), or at their locus of growth.

It has been found that the action of the inventive mixtures goes far beyond the fungicidal and/or insecticidal and/or plant health improving action of the active compounds present in the mixture alone.

Moreover, we have found that simultaneous, that is joint or separate, application of the compound I and compound II or successive application of the compound I and compound II allows enhanced control of pests, that means animal pests, and harmful fungi, compared to the control rates that are possible with the individual compounds (synergistic mixtures, wherein the synergism is pesticidal synergism, i.e. synergistic fungicidal mixtures/synergistic insecticidal mixtures).

Moreover, we have found that simultaneous, that is joint or separate, application of the compound I and compound II or successive application of the compound I and compound II provides enhanced plant health effects compared to the plant health effects that are possible with the individual compounds (synergistic mixtures wherein the synergism is plant health synergism).

Preferably, the mixtures according to the present invention comprise insecticidal compound I selected from alpha-cypermethrin, bifenthrin, cyfluthrin, cypermethrin, deltamethrin, esfenvalerate, etofenprox, fenvalerate, flucythrinate, permethrin and zeta-cypermethrin and as compound II a strobilurine fungicide as defined herein above and below.

More preferably, the mixtures according to the present invention comprise insecticidal compound I selected from alpha-cypermethrin, bifenthrin, cypermethrin, deltamethrin, flucythrinate and permethrin and as compound II a strobilurine fungicide as defined herein above and below.

Most preferably, the mixtures according to the present invention comprise comprise insecticidal compound I selected from alpha-cypermethrin, bifenthrin, cypermethrin and deltamethrin and as compound II a strobilurine fungicide as defined herein above and below.

Utmost preference is given to mixtures comprising insecticidal compound I selected from alpha-cypermethrin and as compound II a strobilurine fungicide as defined herein above and below.

Preferably, the mixtures according to the present invention comprise an insecticidal compound I as defined above as compound II azoxystrobin, dimoxystrobin, enestroburin, fluoxastrobin, kresoxinn-methyl, metominostrobin, orysastrobin, picoxystrobin, pyraclostrobin, pyribencarb or trifloxystrobin. More preferably, the mixtures according to the present invention comprise an insecticidal compound I as defined above and as compound II azoxystrobin, dinnoxystrobin, fluoxastrobin, kresoxim-methyl, picoxystrobin, pyraclostrobin or trifloxystrobin. Most preferably, the mixtures according to the present invention comprise an insecticidal compound I as defined above and as compound II azoxystrobin, pyraclostrobin or trifloxystrobin. Utmost preference is given to mixtures comprising an insecticidal compound I as defined above and pyraclostrobin as compound II.

Thus, the present invention overall comprises and relates to the following mixtures set forth in table 1:

In table 1, the following abbreviations are used herein:

| | |
|---|---|
| I is compound I | PER = permethrin |
| II is compound II | FLU = flucythrinate |
| P = pyraclostrobin | ESFEN = esfenvalerate |
| T = trifloxystrobin | FEN = fenvalerate |
| A = azoxystrobin | ETO = etofenprox |
| F = fluoxastrobin | ZETA = zeta-cypermethrin |
| KM = kresoxim-methyl | AC = acrinathrin |
| PIC = picoxystrobin | ALL = allethrin |
| CMET = coumethoxystrobin | BETA = beta-cypermethrin |
| CMOX = coumoxystrobin | CYFLU = cyfluthrin |
| D = dimoxystrobin | CYPH = cyphenothrin |
| E = enestroburin | DIFLU = dimefluthrin |
| MET = metominostrobin | FPRO = fenpropathrin |
| O = orysastrobin | IMI = imiprothrin |
| PYM = pyrametostrobin | PRAL = prallethrin |
| PYRI = pyribencarb | PRO = profluthrin |
| S-1 = 2-(ortho-((2,5-Dimethylphenyl-oxymethylen)phenyl)-3-methoxy-acrylic acid methyl ester | PY-I = pyrethrin I |
| | PY-II = pyrethrin II |
| | RES = resmethrin |
| S-2 = 2-(2-(3-(2,6-dichlorophenyl)-1-methyl-allylideneaminooxymethyl)-phenyl)-2-methoxyimino-N-methyl-acetamide | SILA = silafluofen |
| | TAU = tau-fluvalinate |
| | TETRA = tetramethrin |
| ALPHA = alpha-cypermethrin | THETA = theta-cypermethrin |
| BIFEN = bifenthrin | TRALO = tralomethrin |
| CYPER = cypermethrin | TRANS = transfluthrin |
| DELTA = deltamethrin | |

TABLE 1

| No. | I | II |
|---|---|---|
| M-1 | ALPHA | P |
| M-2 | ALPHA | T |
| M-3 | ALPHA | A |
| M-4 | ALPHA | F |
| M-5 | ALPHA | KM |
| M-6 | ALPHA | PIC |
| M-7 | ALPHA | CMET |
| M-8 | ALPHA | CMOX |
| M-9 | ALPHA | D |
| M-10 | ALPHA | E |
| M-11 | ALPHA | MET |
| M-12 | ALPHA | O |
| M-13 | ALPHA | PYM |
| M-14 | ALPHA | PYRI |
| M-15 | ALPHA | S-1 |
| M-16 | ALPHA | S-2 |
| M-17 | BIFEN | P |
| M-18 | BIFEN | T |
| M-19 | BIFEN | A |
| M-20 | BIFEN | F |
| M-21 | BIFEN | KM |
| M-22 | BIFEN | PIC |
| M-23 | BIFEN | CMET |
| M-24 | BIFEN | CMOX |
| M-25 | BIFEN | D |
| M-26 | BIFEN | E |
| M-27 | BIFEN | MET |
| M-28 | BIFEN | O |

TABLE 1-continued

| No. | I | II |
| --- | --- | --- |
| M-29 | BIFEN | PYM |
| M-30 | BIFEN | PYRI |
| M-31 | BIFEN | S-1 |
| M-32 | BIFEN | S-2 |
| M-33 | CYPER | P |
| M-34 | CYPER | T |
| M-35 | CYPER | A |
| M-36 | CYPER | F |
| M-37 | CYPER | KM |
| M-38 | CYPER | PIC |
| M-39 | CYPER | CMET |
| M-40 | CYPER | CMOX |
| M-41 | CYPER | D |
| M-42 | CYPER | E |
| M-43 | CYPER | MET |
| M-44 | CYPER | O |
| M-45 | CYPER | PYM |
| M-46 | CYPER | PYRI |
| M-47 | CYPER | S-1 |
| M-48 | CYPER | S-2 |
| M-49 | DELTA | P |
| M-50 | DELTA | T |
| M-51 | DELTA | A |
| M-52 | DELTA | F |
| M-53 | DELTA | KM |
| M-54 | DELTA | PIC |
| M-55 | DELTA | CMET |
| M-56 | DELTA | CMOX |
| M-57 | DELTA | D |
| M-58 | DELTA | E |
| M-59 | DELTA | MET |
| M-60 | DELTA | O |
| M-61 | DELTA | PYM |
| M-62 | DELTA | PYRI |
| M-63 | DELTA | S-1 |
| M-64 | DELTA | S-2 |
| M-65 | FLU | P |
| M-66 | FLU | T |
| M-67 | FLU | A |
| M-68 | FLU | F |
| M-69 | FLU | KM |
| M-70 | FLU | PIC |
| M-71 | FLU | CMET |
| M-72 | FLU | CMOX |
| M-73 | FLU | D |
| M-74 | FLU | E |
| M-75 | FLU | MET |
| M-76 | FLU | O |
| M-77 | FLU | PYM |
| M-78 | FLU | PYRI |
| M-79 | FLU | S-1 |
| M-80 | FLU | S-2 |
| M-81 | PER | P |
| M-82 | PER | T |
| M-83 | PER | A |
| M-84 | PER | F |
| M-85 | PER | KM |
| M-86 | PER | PIC |
| M-87 | PER | CMET |
| M-88 | PER | CMOX |
| M-89 | PER | D |
| M-90 | PER | E |
| M-91 | PER | MET |
| M-92 | PER | O |
| M-93 | PER | PYM |
| M-94 | PER | PYRI |
| M-95 | PER | S-1 |
| M-96 | PER | S-2 |
| M-97 | ESFEN | P |
| M-98 | ESFEN | T |
| M-99 | ESFEN | A |
| M-100 | ESFEN | F |
| M-101 | ESFEN | KM |
| M-102 | ESFEN | PIC |
| M-103 | ESFEN | CMET |
| M-104 | ESFEN | CMOX |
| M-105 | ESFEN | D |
| M-106 | ESFEN | E |
| M-107 | ESFEN | MET |
| M-108 | ESFEN | O |
| M-109 | ESFEN | PYM |
| M-110 | ESFEN | PYRI |
| M-111 | ESFEN | S-1 |
| M-112 | ESFEN | S-2 |
| M-113 | FEN | P |
| M-114 | FEN | T |
| M-115 | FEN | A |
| M-116 | FEN | F |
| M-117 | FEN | KM |
| M-118 | FEN | PIC |
| M-119 | FEN | CMET |
| M-120 | FEN | CMOX |
| M-121 | FEN | D |
| M-122 | FEN | E |
| M-123 | FEN | MET |
| M-124 | FEN | O |
| M-125 | FEN | PYM |
| M-126 | FEN | PYRI |
| M-127 | FEN | S-1 |
| M-128 | FEN | S-2 |
| M-129 | ETO | P |
| M-130 | ETO | T |
| M-131 | ETO | A |
| M-132 | ETO | F |
| M-133 | ETO | KM |
| M-134 | ETO | PIC |
| M-135 | ETO | CMET |
| M-136 | ETO | CMOX |
| M-137 | ETO | D |
| M-138 | ETO | E |
| M-139 | ETO | MET |
| M-140 | ETO | O |
| M-141 | ETO | PYM |
| M-142 | ETO | PYRI |
| M-143 | ETO | S-1 |
| M-144 | ETO | S-2 |
| M-145 | ZETA | P |
| M-146 | ZETA | T |
| M-147 | ZETA | A |
| M-148 | ZETA | F |
| M-149 | ZETA | KM |
| M-150 | ZETA | PIC |
| M-151 | ZETA | CMET |
| M-152 | ZETA | CMOX |
| M-153 | ZETA | D |
| M-154 | ZETA | E |
| M-155 | ZETA | MET |
| M-156 | ZETA | O |
| M-157 | ZETA | PYM |
| M-158 | ZETA | PYRI |
| M-159 | ZETA | S-1 |
| M-160 | ZETA | S-2 |
| M-161 | AC | P |
| M-162 | AC | T |
| M-163 | AC | A |
| M-164 | AC | F |
| M-165 | AC | KM |
| M-166 | AC | PIC |
| M-167 | AC | CMET |
| M-168 | AC | CMOX |
| M-169 | AC | D |
| M-170 | AC | E |
| M-171 | AC | MET |
| M-172 | AC | O |
| M-173 | AC | PYM |
| M-174 | AC | PYRI |
| M-175 | AC | S-1 |
| M-176 | AC | S-2 |
| M-177 | ALL | P |
| M-178 | ALL | T |
| M-179 | ALL | A |
| M-180 | ALL | F |
| M-181 | ALL | KM |
| M-182 | ALL | PIC |
| M-183 | ALL | CMET |
| M-184 | ALL | CMOX |

TABLE 1-continued

| No. | I | II |
|---|---|---|
| M-185 | ALL | D |
| M-186 | ALL | E |
| M-187 | ALL | MET |
| M-188 | ALL | O |
| M-189 | ALL | PYM |
| M-190 | ALL | PYRI |
| M-191 | ALL | S-1 |
| M-192 | ALL | S-2 |
| M-193 | BETA | P |
| M-194 | BETA | T |
| M-195 | BETA | A |
| M-196 | BETA | F |
| M-197 | BETA | KM |
| M-198 | BETA | PIC |
| M-199 | BETA | CMET |
| M-200 | BETA | CMOX |
| M-201 | BETA | D |
| M-202 | BETA | E |
| M-203 | BETA | MET |
| M-204 | BETA | O |
| M-205 | BETA | PYM |
| M-206 | BETA | PYRI |
| M-207 | BETA | S-1 |
| M-208 | BETA | S-2 |
| M-209 | CYFLU | P |
| M-210 | CYFLU | T |
| M-211 | CYFLU | A |
| M-212 | CYFLU | F |
| M-213 | CYFLU | KM |
| M-214 | CYFLU | PIC |
| M-215 | CYFLU | CMET |
| M-216 | CYFLU | CMOX |
| M-217 | CYFLU | D |
| M-218 | CYFLU | E |
| M-219 | CYFLU | MET |
| M-220 | CYFLU | O |
| M-221 | CYFLU | PYM |
| M-222 | CYFLU | PYRI |
| M-223 | CYFLU | S-1 |
| M-224 | CYFLU | S-2 |
| M-225 | CYPH | P |
| M-226 | CYPH | T |
| M-227 | CYPH | A |
| M-228 | CYPH | F |
| M-229 | CYPH | KM |
| M-230 | CYPH | PIC |
| M-231 | CYPH | CMET |
| M-232 | CYPH | CMOX |
| M-233 | CYPH | D |
| M-234 | CYPH | E |
| M-235 | CYPH | MET |
| M-236 | CYPH | O |
| M-237 | CYPH | PYM |
| M-238 | CYPH | PYRI |
| M-239 | CYPH | S-1 |
| M-240 | CYPH | S-2 |
| M-241 | DIFLU | P |
| M-242 | DIFLU | T |
| M-243 | DIFLU | A |
| M-244 | DIFLU | F |
| M-245 | DIFLU | KM |
| M-246 | DIFLU | PIC |
| M-247 | DIFLU | CMET |
| M-248 | DIFLU | CMOX |
| M-249 | DIFLU | D |
| M-250 | DIFLU | E |
| M-251 | DIFLU | MET |
| M-252 | DIFLU | O |
| M-253 | DIFLU | PYM |
| M-254 | DIFLU | PYRI |
| M-255 | DIFLU | S-1 |
| M-256 | DIFLU | S-2 |
| M-257 | FPRO | P |
| M-258 | FPRO | T |
| M-259 | FPRO | A |
| M-260 | FPRO | F |
| M-261 | FPRO | KM |
| M-262 | FPRO | PIC |
| M-263 | FPRO | CMET |
| M-264 | FPRO | CMOX |
| M-265 | FPRO | D |
| M-266 | FPRO | E |
| M-267 | FPRO | MET |
| M-268 | FPRO | O |
| M-269 | FPRO | PYM |
| M-270 | FPRO | PYRI |
| M-271 | FPRO | S-1 |
| M-272 | FPRO | S-2 |
| M-273 | IMI | P |
| M-274 | IMI | T |
| M-275 | IMI | A |
| M-276 | IMI | F |
| M-277 | IMI | KM |
| M-278 | IMI | PIC |
| M-279 | IMI | CMET |
| M-280 | IMI | CMOX |
| M-281 | IMI | D |
| M-282 | IMI | E |
| M-283 | IMI | MET |
| M-284 | IMI | O |
| M-285 | IMI | PYM |
| M-286 | IMI | PYRI |
| M-287 | IMI | S-1 |
| M-288 | IMI | S-2 |
| M-289 | PRAL | P |
| M-290 | PRAL | T |
| M-291 | PRAL | A |
| M-292 | PRAL | F |
| M-293 | PRAL | KM |
| M-294 | PRAL | PIC |
| M-295 | PRAL | CMET |
| M-296 | PRAL | CMOX |
| M-297 | PRAL | D |
| M-298 | PRAL | E |
| M-299 | PRAL | MET |
| M-300 | PRAL | O |
| M-301 | PRAL | PYM |
| M-302 | PRAL | PYRI |
| M-303 | PRAL | S-1 |
| M-304 | PRAL | S-2 |
| M-305 | PRO | P |
| M-306 | PRO | T |
| M-307 | PRO | A |
| M-308 | PRO | F |
| M-309 | PRO | KM |
| M-310 | PRO | PIC |
| M-311 | PRO | CMET |
| M-312 | PRO | CMOX |
| M-313 | PRO | D |
| M-314 | PRO | E |
| M-315 | PRO | MET |
| M-316 | PRO | O |
| M-317 | PRO | PYM |
| M-318 | PRO | PYRI |
| M-319 | PRO | S-1 |
| M-320 | PRO | S-2 |
| M-321 | PY-I | P |
| M-322 | PY-I | T |
| M-323 | PY-I | A |
| M-324 | PY-I | F |
| M-325 | PY-I | KM |
| M-326 | PY-I | PIC |
| M-327 | PY-I | CMET |
| M-328 | PY-I | CMOX |
| M-329 | PY-I | D |
| M-330 | PY-I | E |
| M-331 | PY-I | MET |
| M-332 | PY-I | O |
| M-333 | PY-I | PYM |
| M-334 | PY-I | PYRI |
| M-335 | PY-I | S-1 |
| M-336 | PY-I | S-2 |
| M-337 | PY-II | P |
| M-338 | PY-II | T |
| M-339 | PY-II | A |
| M-340 | PY-II | F |

TABLE 1-continued

| No. | I | II |
|---|---|---|
| M-341 | PY-II | KM |
| M-342 | PY-II | PIC |
| M-343 | PY-II | CMET |
| M-344 | PY-II | CMOX |
| M-345 | PY-II | D |
| M-346 | PY-II | E |
| M-347 | PY-II | MET |
| M-348 | PY-II | O |
| M-349 | PY-II | PYM |
| M-350 | PY-II | PYRI |
| M-351 | PY-II | S-1 |
| M-352 | PY-II | S-2 |
| M-353 | RES | P |
| M-354 | RES | T |
| M-355 | RES | A |
| M-356 | RES | F |
| M-357 | RES | KM |
| M-358 | RES | PIC |
| M-359 | RES | CMET |
| M-360 | RES | CMOX |
| M-361 | RES | D |
| M-362 | RES | E |
| M-363 | RES | MET |
| M-364 | RES | O |
| M-365 | RES | PYM |
| M-366 | RES | PYRI |
| M-367 | RES | S-1 |
| M-368 | RES | S-2 |
| M-369 | SILA | P |
| M-370 | SILA | T |
| M-371 | SILA | A |
| M-372 | SILA | F |
| M-373 | SILA | KM |
| M-374 | SILA | PIC |
| M-375 | SILA | CMET |
| M-376 | SILA | CMOX |
| M-377 | SILA | D |
| M-378 | SILA | E |
| M-379 | SILA | MET |
| M-380 | SILA | O |
| M-381 | SILA | PYM |
| M-382 | SILA | PYRI |
| M-383 | SILA | S-1 |
| M-384 | SILA | S-2 |
| M-385 | TAU | P |
| M-386 | TAU | T |
| M-387 | TAU | A |
| M-388 | TAU | F |
| M-389 | TAU | KM |
| M-390 | TAU | PIC |
| M-391 | TAU | CMET |
| M-392 | TAU | CMOX |
| M-393 | TAU | D |
| M-394 | TAU | E |
| M-395 | TAU | MET |
| M-396 | TAU | O |
| M-397 | TAU | PYM |
| M-398 | TAU | PYRI |
| M-399 | TAU | S-1 |
| M-400 | TAU | S-2 |
| M-401 | TETRA | P |
| M-402 | TETRA | T |
| M-403 | TETRA | A |
| M-404 | TETRA | F |
| M-405 | TETRA | KM |
| M-406 | TETRA | PIC |
| M-407 | TETRA | CMET |
| M-408 | TETRA | CMOX |
| M-409 | TETRA | D |
| M-410 | TETRA | E |
| M-411 | TETRA | MET |
| M-412 | TETRA | O |
| M-413 | TETRA | PYM |
| M-414 | TETRA | PYRI |
| M-415 | TETRA | S-1 |
| M-416 | TETRA | S-2 |
| M-417 | THETA | P |
| M-418 | THETA | T |
| M-419 | THETA | A |
| M-420 | THETA | F |
| M-421 | THETA | KM |
| M-422 | THETA | PIC |
| M-423 | THETA | CMET |
| M-424 | THETA | CMOX |
| M-425 | THETA | D |
| M-426 | THETA | E |
| M-427 | THETA | MET |
| M-428 | THETA | O |
| M-429 | THETA | PYM |
| M-430 | THETA | PYRI |
| M-431 | THETA | S-1 |
| M-432 | THETA | S-2 |
| M-433 | TRALO | P |
| M-434 | TRALO | T |
| M-435 | TRALO | A |
| M-436 | TRALO | F |
| M-437 | TRALO | KM |
| M-438 | TRALO | PIC |
| M-439 | TRALO | CMET |
| M-440 | TRALO | CMOX |
| M-441 | TRALO | D |
| M-442 | TRALO | E |
| M-443 | TRALO | MET |
| M-444 | TRALO | O |
| M-445 | TRALO | PYM |
| M-446 | TRALO | PYRI |
| M-447 | TRALO | S-1 |
| M-448 | TRALO | S-2 |
| M-449 | TRANS | P |
| M-450 | TRANS | T |
| M-451 | TRANS | A |
| M-452 | TRANS | F |
| M-453 | TRANS | KM |
| M-454 | TRANS | PIC |
| M-455 | TRANS | CMET |
| M-456 | TRANS | CMOX |
| M-457 | TRANS | D |
| M-458 | TRANS | E |
| M-459 | TRANS | MET |
| M-460 | TRANS | O |
| M-461 | TRANS | PYM |
| M-462 | TRANS | PYRI |
| M-463 | TRANS | S-1 |
| M-464 | TRANS | S-2 |

Within the mixtures of table 1, the following mixtures are preferred: M-1, M-2, M-3, M-4, M-5, M-6, M-17, M-18, M-19, M-20, M-21, M-22, M-33, M-34, M-35, M-36, M-37, M-38, M-49, M-50, M-51, M-52, M-53, M-54, M-65, M-66, M-67, M-68, M-69, M-70, M-81, M-82, M-83, M-84, M-85 and M-86. Within the above-mentioned preferred subset of mixtures, the following mixtures are preferred: M-1, M-2, M-3, M-17, M-18, M-19, M-33, M-34, M-35, M-49, M-50, M-51, M-65, M-66, M-67, M-81, M-82, M-83M-97, M-98, M-99, M-113, M-114, M-115, M-129, M-130, M-131M-145, M-146, M-147, M-161, M-162 and M-163; the following mixtures M-1, M-2, M-3, M-17, M-18, M-19, M-33, M-34, M-35, M-49, M-50 and M-51 are more preferred and the mixtures M-1, M-2, M-17, M-18, M-33, M-34, M-49 and M-50 are most preferred. Herein, particular preference is given to M-1, M-17, M-33 and M-49 and utmost preference is given to M1.

The ratios by weight for the each of the above-referred mixtures comprising inseciticdal compound I and the fungicidal compound II are from 1:500 to 500:1, preferably from 1:100 to 100:1, more preferably from 1:25 to 25:1 and most preferably from 1:10 to 10:1.

In a further embodiment, the present invention also relates to mixtures comprising
1) one insecticidal compound I selected from cyhalothrin, tefluthrin and lambdacyhalothrin; and 2) one fungicidal compound II selected from the group of coumethoxystrobin, coumoxystrobin, dimoxystrobin, enestroburin, fluoxastrobin, kresoxim-methyl, metominostrobin, orysastrobin, picoxystrobin, pyraclostrobin, pyrametostrobin, pyraoxystrobin, pyribencarb, trifloxystrobin, 2-(ortho-((2,5-Dimethylphenyl-oxymethylen)phenyl)-3-methoxy-acrylic acid methyl ester, 2-(2-(3-(2,6-dichlorophenyl)-1-methyl-allylideneaminooxymethylyphenyl)-2-methoxyimino-N-methyl-acetamide;

in synergistic effective amounts, wherein, preferably, these mixtures comprise as compound II azoxystrobin, dimoxystrobin, enestroburin, fluoxastrobin, kresoxim-methyl, metominostrobin, orysastrobin, picoxystrobin, pyraclostrobin, pyribencarb or trifloxystrobin, more preferably as compound II dimoxystrobin, fluoxastrobin, kresoxim-methyl, picoxystrobin, pyraclostrobin or trifloxystrobin, most preferably, azoxystrobin, pyraclostrobin or trifloxystrobin, utmost preferably and pyraclostrobin as compound II.

All afore-mentioned mixtures (N-1 to N-42) including the preferred [N-16 to N-42], more preferred [N-25 to N-42], most preferred [N-36 to N-42] and utmost preferred embodiments [N-39 to N-42] of these mixtures are set forth in table 2:

| | |
|---|---|
| I is compound I | O = orysastrobin |
| II is compound II | PYM = pyrametostrobin |
| P = pyraclostrobin | PYRI = pyribencarb |
| T = trifloxystrobin | S-1 = 2-(ortho-((2,5-Dimethylphenyl- |
| F = fluoxastrobin | oxymethylen)phenyl)-3-methoxy-acrylic acid |
| KM = kresoxim-methyl | methyl ester |
| PIC = picoxystrobin | S-2 = 2-(2-(3-(2,6-dichlorophenyl)-1-methyl- |
| CMET = coumethoxystrobin | allylideneaminooxymethyl)-phenyl)-2- |
| CMOX = coumoxystrobin | methoxyimino-N-methyl-acetamide |
| D = dimoxystrobin | CY = cyhalothrin, |
| E = enestroburin | TE = tefluthrin |
| MET = metominostrobin | L-CY = lambda-cyhalothrin |

| No. | I | II |
|---|---|---|
| N-1 | CY | S-1 |
| N-2 | TE | S-1 |
| N-3 | L-CY | S-1 |
| N-4 | CY | S-2 |
| N-5 | TE | S-2 |
| N-6 | L-CY | S-2 |
| N-7 | CY | CMOX |
| N-8 | TE | CMOX |
| N-9 | L-CY | CMOX |
| N-10 | CY | CMET |
| N-11 | TE | CMET |
| N-12 | L-CY | CMET |
| N-13 | CY | PYM |
| N-14 | TE | PYM |
| N-15 | L-CY | PYM |
| N-16 | CY | E |
| N-17 | TE | E |
| N-18 | L-CY | E |
| N-19 | CY | MET |
| N-20 | TE | MET |
| N-21 | L-CY | MET |
| N-22 | CY | O |
| N-23 | TE | O |
| N-24 | L-CY | O |
| N-25 | CY | D |
| N-26 | TE | D |
| N-27 | L-CY | D |
| N-28 | CY | PIC |
| N-29 | TE | PIC |
| N-30 | L-CY | PIC |
| N-31 | CY | KM |
| N-32 | TE | KM |
| N-33 | L-CY | KM |
| N-34 | CY | F |
| N-35 | TE | F |
| N-36 | L-CY | F |
| N-37 | CY | T |
| N-38 | TE | T |
| N-39 | L-CY | T |
| N-40 | CY | P |
| N-41 | TE | P |
| N-42 | L-CY | P |

Herein, in accordance with the above-mentioned preferences, the following mixtures of table 2 are preferred: N-16, N-17, N-18, N-19, N-20, N-21, N-22, N-23, N-24, N-25, N-26, N-27, N-28, N-29, N-30, N-31, N-32, N-33, N-34, N-35, N-36, N-37, N-38, N-39, N-40, N-41 and N-42; the following mixtures N-26, N-27, N-28, N-29, N-30, N-31, N-32, N-33, N-34, N-35, N-36, N-37, N-38, N-39, N-40, N-41 and N-42 are more preferred and the mixtures N-37, N-38, N-39, N-40, N-41 and N-42 are most preferred. Herein, utmost preference is given to N-40, N-41 and N-42.

The ratios by weight for the each of the above-referred mixtures comprising inseciticdal compound I and the fungicidal compound II are from 1:500 to 500:1, preferably from 1:100 to 100:1, more preferably from 1:25 to 25:1 and most preferably from 1:10 to 10:1.

Each of the above-mentioned inventive mixtures can further comprise one or more insecticides, fungicides, herbicides.

For use according to the present invention, the mixtures according to the invention can be converted into the customary formulations, for example solutions, emulsions, suspensions, dusts, powders, pastes and granules. The use form depends on the particular intended purpose; in each case, it should ensure a fine and even distribution of the mixtures according to the present invention. The formulations are prepared in a known manner (cf. U.S. Pat. No. 3,060,084, EP-A 707 445 (for liquid concentrates), Browning: "Agglomeration", Chemical Engineering, Dec. 4, 1967, 147-48, Perry's Chemical Engineer's Handbook, 4th Ed., McGraw-Hill, New York, 1963, S. 8-57 and ff. WO 91/13546, U.S. Pat. Nos. 4,172,714, 4,144,050, 3,920,442, 5,180,587, 5,232,701, 5,208,030, GB 2,095,558, U.S. Pat. No. 3,299,566, Klingman: Weed Control as a Science (J. Wiley & Sons, New York, 1961), Hance et al.: Weed Control Handbook (8th Ed., Blackwell Scientific, Oxford, 1989) and Mollet, H. and Grubemann, A.: Formulation technology (Wiley VCH Verlag, Weinheim, 2001).

The agrochemical formulations may also comprise auxiliaries which are customary in agrochemical formulations. The auxiliaries used depend on the particular application form and active substance, respectively.

Examples for suitable auxiliaries are solvents, solid carriers, dispersants or emulsifiers (such as further solubilizers, protective colloids, surfactants and adhesion agents), organic and anorganic thickeners, bactericides, anti-freezing agents, anti-foaming agents, if appropriate colorants and tackifiers or binders (e.g. for seed treatment formulations).

Suitable solvents are water, organic solvents such as mineral oil fractions of medium to high boiling point, such as kerosene or diesel oil, furthermore coal tar oils and oils of vegetable or animal origin, aliphatic, cyclic and aromatic hydrocarbons, e.g. toluene, xylene, paraffin, tetrahydronaphthalene, alkylated naphthalenes or their derivatives, alcohols such as methanol, ethanol, propanol, butanol and cyclohexanol, glycols, ketones such as cyclohexanone and gamma-butyrolactone, fatty acid dimethylamides, fatty acids and fatty acid esters and strongly polar solvents, e.g. amines such as N-methylpyrrolidone.

Solid carriers are mineral earths such as silicates, silica gels, talc, kaolins, limestone, lime, chalk, bole, loess, clays, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Suitable surfactants (adjuvants, wtters, tackifiers, dispersants or emulsifiers) are alkali metal, alkaline earth metal and ammonium salts of aromatic sulfonic acids, such as ligninsoulfonic acid (Borresperse® types, Borregard, Norway) phenolsulfonic acid, naphthalenesulfonic acid (Morwet® types, Akzo Nobel, U.S.A.), dibutylnaphthalene-sulfonic acid (Nekal® types, BASF, Germany), and fatty acids, alkylsulfonates, alkyl-arylsulfonates, alkyl sulfates, laurylether sulfates, fatty alcohol sulfates, and sulfated hexa-, hepta- and octadecanolates, sulfated fatty alcohol glycol ethers, furthermore condensates of naphthalene or of naphthalenesulfonic acid with phenol and formaldehyde, poly-oxy-ethylene octylphenyl ether, ethoxylated isooctylphenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and proteins, denatured proteins, polysaccharides (e.g. methylcellulose), hydrophobically modified starches, polyvinyl alcohols (Mowiol® types, Clariant, Switzerland), polycarboxylates (Sokolan® types, BASF, Germany), polyalkoxylates, polyvinylamines (Lupasol® types, BASF, Germany), polyvinylpyrrolidone and the copolymers thereof.

Examples for thickeners (i.e. compounds that impart a modified flowability to formulations, i.e. high viscosity under static conditions and low viscosity during agitation) are polysaccharides and organic and anorganic clays such as Xanthan gum (Kelzan®, CP Kelco, U.S.A.), Rhodopol® 23 (Rhodia, France), Veegum® (R. T. Vanderbilt, U.S.A.) or Attaclay® (Engelhard Corp., NJ, USA).

Bactericides may be added for preservation and stabilization of the formulation. Examples for suitable bactericides are those based on dichlorophene and benzylalcohol hemi formal (Proxel® from ICI or Acticide® RS from Thor Chemie and Kathon® MK from Rohm & Haas) and isothiazolinone derivatives such as alkylisothiazolinones and benzisothiazolinones (Acticide® MBS from Thor Chemie).

Examples for suitable anti-freezing agents are ethylene glycol, propylene glycol, urea and glycerin.

Examples for anti-foaming agents are silicone emulsions (such as e.g. Silikon® SRE, Wacker, Germany or Rhodorsil®, Rhodia, France), long chain alcohols, fatty acids, salts of fatty acids, fluoroorganic compounds and mixtures thereof.

Suitable colorants are pigments of low water solubility and water-soluble dyes. Examples to be mentioned and the designations rhodamin B, C. I. pigment red 112, C. I. solvent red 1, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108. Examples for tackifiers or binders are polyvinylpyrrolidons, polyvinylacetates, polyvinyl alcohols and cellulose ethers (Tylose®, Shin-Etsu, Japan).

Powders, materials for spreading and dusts can be prepared by mixing or concomitantly grinding the compounds the resepective active compounds present in the inventive mixtures and, if appropriate, further active substances, with at least one solid carrier.

Granules, e.g. coated granules, impregnated granules and homogeneous granules, can be prepared by binding the active substances to solid carriers. Examples of solid carriers are mineral earths such as silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, such as, e.g., ammonium sulfate, ammonium phosphate, ammonium nitrate, ureas, and products of vegetable origin, such as cereal meal, tree bark meal, wood meal and nutshell meal, cellulose powders and other solid carriers.

Examples of formulation types are suspensions (SC, OD, FS), emulsifiable concentrates (EC), emulsions (EW, EO, ES), pastes, pastilles, wettable powders or dusts (WP, SP, SS, WS, DP, DS) or granules (GR, FG, GG, MG), which can be water-soluble or wettable, as well as gel formulations for the treatment of plant propagation materials such as seeds (GF), herein further below exemplified in detail:

1. Composition types for dilution with water
i) Water-soluble concentrates (SL, LS)

10 parts by weight of compounds of the inventive mixtures are dissolved in 90 parts by weight of water or in a water-soluble solvent. As an alternative, wetting agents or other auxiliaries are added. The active substance dissolves upon dilution with water. In this way, a formulation having a content of 10% by weight of active substance is obtained.

ii) Dispersible concentrates (DC)

20 parts by weight of compounds of the inventive mixtures are dissolved in 70 parts by weight of cyclohexanone with addition of 10 parts by weight of a dispersant, e.g. polyvinylpyrrolidone. Dilution with water gives a dispersion. The active substance content is 20% by weight.

iii) Emulsifiable concentrates (EC)

15 parts by weight of compounds of the inventive mixtures are dissolved in 75 parts by weight of xylene with addition of calcium dodecylbenzenesulfonate and castor oil ethoxylate (in each case 5 parts by weight). Dilution with water gives an emulsion. The composition has an active substance content of 15% by weight.

iv) Emulsions (EW, EO, ES)

25 parts by weight of compounds of the inventive mixtures are dissolved in 35 parts by weight of xylene with addition of calcium dodecylbenzenesulfonate and castor oil ethoxylate (in each case 5 parts by weight). This mixture is introduced into 30 parts by weight of water by means of an emulsifying machine (Ultraturrax) and made into a homogeneous emulsion. Dilution with water gives an emulsion. The composition has an active substance content of 25% by weight.

v) Suspensions (SC, OD, FS)

In an agitated ball mill, 20 parts by weight of compounds of the inventive mixtures are comminuted with addition of 10 parts by weight of dispersants and wetting agents and 70 parts by weight of water or an organic solvent to give a fine active substance suspension. Dilution with water gives a stable suspension of the active substance. The active substance content in the composition is 20% by weight.

vi) Water-dispersible granules and water-soluble granules (WG, SG)

50 parts by weight of compounds of the inventive mixtures are ground finely with addition of 50 parts by weight of dispersants and wetting agents and prepared as water-dispersible or water-soluble granules by means of technical appliances (e.g. extrusion, spray tower, fluidized bed). Dilution with water gives a stable dispersion or solution of the active substance. The composition has an active substance content of 50% by weight.

vii) Water-dispersible powders and water-soluble powders (WP, SP, SS, WS)

75 parts by weight of compounds of the inventive mixtures are ground in a rotor-stator mill with addition of 25 parts by weight of dispersants, wetting agents and silica gel. Dilution with water gives a stable dispersion or solution of the active substance. The active substance content of the composition is 75% by weight.

viii) Gel (GF)

In an agitated ball mill, 20 parts by weight of compounds of the inventive mixtures are comminuted with addition of 10 parts by weight of dispersants, 1 part by weight of a gelling agent wetters and 70 parts by weight of water or of an organic solvent to give a fine suspension of the active substance. Dilution with water gives a stable suspension of the active substance, whereby a composition with 20% (w/w) of active substance is obtained.

2. Composition types to be applied undiluted ix) Dustable powders (DP, DS)

5 parts by weight of compounds of the inventive mixtures are ground finely and mixed intimately with 95 parts by weight of finely divided kaolin. This gives a dustable composition having an active substance content of 5% by weight.

x) Granules (GR, FG, GG, MG)

0.5 parts by weight of compounds of the inventive mixtures is ground finely and associated with 99.5 parts by weight of carriers. Current methods are extrusion, spray-drying or the fluidized bed. This gives granules to be applied undiluted having an active substance content of 0.5% by weight.

xi) ULV solutions (UL)

10 parts by weight of compounds of the inventive mixtures are dissolved in 90 parts by weight of an organic solvent, e.g. xylene. This gives a composition to be applied undiluted having an active substance content of 10% by weight.

The agrochemical formulations generally comprise between 0.01 and 95%, preferably between 0.1 and 90%, most preferably between 0.5 and 90%, by weight of active substances. The compounds of the inventive mixtures are employed in a purity of from 90% to 100%, preferably from 95% to 100% (according to NMR spectrum).

The compounds of the inventive mixtures can be used as such or in the form of their compositions, e.g. in the form of directly sprayable solutions, powders, suspensions, dispersions, emulsions, oil dispersions, pastes, dustable products, materials for spreading, or granules, by means of spraying, atomizing, dusting, spreading, brushing, immersing or pouring. The application forms depend entirely on the intended purposes; it is intended to ensure in each case the finest possible distribution of the compounds present in the inventive mixtures.

Aqueous application forms can be prepared from emulsion concentrates, pastes or wettable powders (sprayable powders, oil dispersions) by adding water. To prepare emulsions, pastes or oil dispersions, the substances, as such or dissolved in an oil or solvent, can be homogenized in water by means of a wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active substance concentrations in the ready-to-use preparations can be varied within relatively wide ranges. In general, they are from 0.0001 to 10%, preferably from 0.001 to 1% by weight of compounds of the inventive mixtures.

The compounds of the inventive mixtures may also be used successfully in the ultra-low-volume process (ULV), it being possible to apply compositions comprising over 95% by weight of active substance, or even to apply the active substance without additives.

Various types of oils, wetters, adjuvants, herbicides, fungicides, other pesticides, or bactericides may be added to the active compounds, if appropriate not until immediately prior to use (tank mix). These agents can be admixed with the compounds of the inventive mixtures in a weight ratio of 1:100 to 100:1, preferably 1:10 to 10:1.

Compositions of this invention may also contain fertilizers such as ammonium nitrate, urea, potash, and superphosphate, phytotoxicants and plant growth regulators and safeners. These may be used sequentially or in combination with the above-described compositions, if appropriate also added only immediately prior to use (tank mix). For example, the plant(s) may be sprayed with a composition of this invention either before or after being treated with the fertilizers.

The compounds contained in the mixtures as defined above can be applied simultaneously, that is jointly or separately, or in succession, wherein the time interval between the individual applications is selected to ensure that the active substance applied first still occurs at the site of action in a sufficient amount at the time of application of the further active substance(s). The order of application is not essential for working of the present invention.

According to this invention, the compound I and compound II is to be understood to denote, that at least the compound I and compound II occur simultaneously at the site of action (i.e. the pests, such as harmful fungi and anminal pests such as insects, arachinds or nematods to be controlled or their habitats such as infected plants, plant propagation materials, particularly seeds, surfaces, materials or the soil as well as plants, plant propagation materials, particularly seeds, soil, surfaces, materials or rooms to be protected from fungal or animal attack) in a effective amount.

This can be obtained by applying the compound I and compound II simultaneously, either jointly (e.g. as tank-mix) or separately, or in succession, wherein the time interval between the individual applications is selected to ensure that the active substance applied first still occurs at the site of action in a sufficient amount at the time of application of the further active substance(s). The order of application is not essential for working of the present invention.

In the mixtures of the present invention, the weight ratio of the compounds generally depends from the properties of the compounds of the inventive mixtures.

The compounds of the inventive mixtures can be used individually or already partially or completely mixed with one another to prepare the composition according to the invention. It is also possible for them to be packaged and used further as combination composition such as a kit of parts.

In one embodiment of the invention, the kits may include one or more, including all, components that may be used to prepare a subject agrochemical composition. E.g., kits may include the compound I and compound II and/or an adjuvant component and/or a further pesticidal compound (e.g. insecticide or herbicide) and/or a growth regulator component). One or more of the components may already be combined together or pre-formulated. In those embodiments where more than two components are provided in a kit, the components may already be combined together and as such are packaged in a single container such as a vial, bottle, can, pouch, bag or canister. In other embodiments, two or more components of a kit may be packaged separately, i.e., not pre-formulated. As such, kits may include one or more separate containers such as vials, cans, bottles, pouches, bags or canisters, each container containing a separate component for an agrochemical composition. In both forms, a component of the kit may be applied separately from or together with the further components or as a component of a combination composition according to the invention for preparing the composition according to the invention.

The user applies the composition according to the invention usually from a predosage device, a knapsack sprayer, a spray tank or a spray plane. Here, the agrochemical composition is made up with water and/or buffer to the desired application concentration, it being possible, if appropriate, to add further auxiliaries, and the ready-to-use spray liquor or the agrochemical composition according to the invention is thus obtained. Usually, 50 to 500 liters of the ready-to-use spray liquor are applied per hectare of agricultural useful area, preferably 100 to 400 liters.

According to one embodiment, individual compounds of the inventive mixtures formulated as composition (or formulation) such as parts of a kit or parts of the inventive mixture may be mixed by the user himself in a spray tank and further auxiliaries may be added, if appropriate (tank mix).

In a further embodiment, either individual compounds of the inventive mixtures formulated as composition or partially premixed components, e.g. components comprising the compound I and compound II may be mixed by the user in a spray tank and further auxiliaries and additives may be added, if appropriate (tank mix).

In a further embodiment, either individual components of the composition according to the invention or partially premixed components, e.g. components comprising the compound I and compound II, can be applied jointly (e.g. after tankmix) or consecutively.

As said above, the present invention comprises a method for controlling pests, that means animal pests and harmful fungi, wherein the pest, their habitat, breeding grounds, their locus or the plants to be protected against pest attack, the soil or plant propagation material (preferably seed) are treated with an pesticidally effective amount of a mixture.

Advantageously, the inventive mixtures are suitable for controlling the following harmful fungi:

*Albugo* spp. (white rust) on ornamentals, vegetables (e.g. *A. candida*) and sunflowers (e.g. *A. tragopogonis*); *Alternaria* spp. (*Alternaria* leaf spot) on vegetables, rape (*A. brassicola* or *brassicae*), sugar beets (*A. tenuis*), fruits, rice, soybeans, potatoes (e.g. *A. solani* or *A. alternata*), tomatoes (e.g. *A. solani* or *A. alternata*) and wheat; *Aphanomyces* spp. on sugar beets and vegetables; *Ascochyta* spp. on cereals and vegetables, e.g. *A. tritici* (anthracnose) on wheat and *A. hordei* on barley; *Bipolaris* and *Drechslera* spp. (teleomorph: *Cochliobolus* spp.), e.g. Southern leaf blight (*D. maydis*) or Northern leaf blight (*B. zeicola*) on corn, e.g. spot blotch (*B. sorokiniana*) on cereals and e.g. *B. oryzae* on rice and turfs; *Blumeria* (formerly *Erysiphe*) *graminis* (powdery mildew) on cereals (e.g. on wheat or barley); *Botrytis cinerea* (teleomorph: *Botryotinia fuceliana*: grey mold) on fruits and berries (e.g. strawberries), vegetables (e.g. lettuce, carrots, celery and cabbages), rape, flowers, vines, forestry plants and wheat; *Bremia lactucae* (downy mildew) on lettuce; *Ceratocystis* (syn. *Ophiostoma*) spp. (rot or wilt) on broad-leaved trees and evergreens, e.g. *C. ulmi* (Dutch elm disease) on elms; *Cercospora* spp. (*Cercospora* leaf spots) on corn (e.g. Gray leaf spot: *C. zeae-maydis*), rice, sugar beets (e.g. *C. beticola*), sugar cane, vegetables, coffee, soybeans (e.g. *C. sojina* or *C. kikuchii*) and rice; *Cladosporium* spp. on tomatoes (e.g. *C. fulvum*: leaf mold) and cereals, e.g. *C. herbarum* (black ear) on wheat; *Claviceps purpurea* (ergot) on cereals; *Cochliobolus* (anamorph: *Helminthosporium* of *Bipolaris*) spp. (leaf spots) on corn (*C. carbonum*), cereals (e.g. *C. sativus*, anamorph: *B. sorokiniana*) and rice (e.g. *C. miyabeanus*, anamorph: *H. oryzae*); *Colletotrichum* (teleomorph: *Glomerella*) spp. (anthracnose) on cotton (e.g. *C. gossypii*), corn (e.g. *C. graminicola*: Anthracnose stalk rot), soft fruits, potatoes (e.g. *C. coccodes* black dot), beans (e.g. *C. lindemuthianum*) and soybeans (e.g. *C. truncatum* or *C. gloeosporioldes*); *Corticium* spp., e.g. *C. sasakii* (sheath blight) on rice; *Corynespora cassilcola* (leaf spots) on soybeans and ornamentals; *Cycloconium* spp., e.g. *C. oleaginum* on olive trees; *Cylindrocarpon* spp. (e.g. fruit tree canker or young vine decline, teleomorph: *Nectria* or *Neonectria* spp.) on fruit trees, vines (e.g. *C. liriodendri*, teleomorph: *Neonectria liriodendri*. Black Foot Disease) and ornamentals; *Dematophora* (teleomorph: *Rosellinia*) necatrix (root and stem rot) on soybeans; *Diaporthe* spp., e.g. *D. phaseolorum* (damping off) on soybeans; *Drechslera* (syn. *Helminthosporium*, teleomorph: *Pyrenophora*) spp. on corn, cereals, such as barley (e.g. *D. teres*, net blotch) and wheat (e.g. *D. tritici-repentis*: tan spot), rice and turf; Esca (dieback, apoplexy) on vines, caused by *Formitiporia* (syn. *Phellinus*) *punctata*, *F. mediterranea*, *Phaeomoniella chlamydospora* (earlier *Phaeoacremonium chlamydosporum*), *Phaeoacremonium aleophilum* and/or *Botryosphaeria obtusa*; *Elsinoe* spp. on pome fruits (*E. pyri*), soft fruits (*E. veneta*: anthracnose) and vines (*E. ampelina*: anthracnose); *Entyloma oryzae* (leaf smut) on rice; *Epicoccum* spp. (black mold) on wheat; *Erysiphe* spp. (powdery mildew) on sugar beets (*E. betae*), vegetables (e.g. *E. pisi*), such as cucurbits (e.g. *E. cichoracearum*), cabbages, rape (e.g. *E. cruciferarum*); *Eutypa lata* (Eutypa canker or dieback, anamorph: *Cytosporina lata*, syn. *Libertella blepharis*) on fruit trees, vines and ornamental woods; *Exserohilum* (syn. *Helminthosporium*) spp. on corn (e.g. *E. turcicum*); *Fusarium* (teleomorph: *Gibberella*) spp. (wilt, root or stem rot) on various plants, such as *F. graminearum* or *F. culmorum* (root rot, scab or head blight) on cereals (e.g. wheat or barley), *F. oxysporum* on tomatoes, *F. solani* on soybeans and *F. verticillioides* on corn; *Gaeumannomyces graminis* (take-all) on cereals (e.g. wheat or barley) and corn; *Gibberella* spp. on cereals (e.g. *G. zeae*) and rice (e.g. *G. fujikuroi*: Bakanae disease); *Glomerella cingulata* on vines, pome fruits and other plants and *G. gossypii* on cotton; Grain-staining complex on rice; *Guignardia bidwellii*(black rot) on vines; *Gymnosporangium* spp. on rosaceous plants and junipers, e.g. *G. sabinae* (rust) on pears; *Helminthosporium* spp. (syn. *Drechslera*, teleomorph: *Cochliobolus*) on corn, cereals and rice; *Hemilela* spp., e.g. *H. vastatrix* (coffee leaf rust) on coffee; *Isariopsis clavispora* (syn. *Cladosporium vitis*) on vines; *Macrophomina phaseolina* (syn. *phaseoli*) (root and stem rot) on soybeans and cotton; *Microdochium* (syn. *Fusarium*) *nivale* (pink snow mold) on cereals (e.g. wheat or barley); *Microsphaera diffusa* (powdery mildew) on soybeans; *Monilinia* spp., e.g. *M. laxa*, *M. fructicola* and *M. fructigena* (bloom and twig blight, brown rot) on stone fruits and other rosaceous plants; *Mycosphaerella* spp. on cereals, bananas, soft fruits and ground nuts, such as e.g. *M. graminicola* (anamorph: *Septoria tritici*, *Septoria* blotch) on wheat or *M. fijiensis* (black Sigatoka disease) on bananas; *Peronospora* spp. (downy mildew) on cabbage (e.g. *P. brassicae*), rape (e.g. *P. parasilica*), onions (e.g. *P. destructor*), tobacco (*P. tabacina*) and soybeans (e.g. *P. manshurica*); *Phakopsora pachyrhizi* and *P. meibomiae* (soybean rust) on soybeans; *Phialophora* spp. e.g. on vines (e.g. *P. tracheiphila* and *P. tetraspora*) and soybeans (e.g. *P. gregata*: stem rot); *Phoma lingam* (root and stem rot) on rape and cabbage and *P. betae* (root rot, leaf spot and damping-off) on sugar beets; *Phomopsis* spp. on sunflowers, vines (e.g. *P. viticola*: can and leaf spot) and soybeans (e.g. stem rot: *P. phaseoli*, teleomorph: *Diaporthe* phaseolorum); *Physoderma maydis* (brown spots) on corn; *Phytophthora* spp. (wilt, root, leaf, fruit and stem root) on various plants, such as paprika and cucurbits (e.g. *P. capsid*), soybeans (e.g. *P. megasperma*, syn. *P. sojae*), potatoes and tomatoes (e.g. *P. Infestans* late blight) and broad-leaved trees (e.g. *P. ramorum*: sudden oak death); *Plasmodiophora brassicae* (club root) on cabbage, rape, radish and other plants; *Plasmopara* spp., e.g. *P. viticola* (grapevine downy mildew) on vines and *P. halstedii* on sunflowers; *Podosphaera* spp. (powdery mildew) on rosaceous plants, hop, pome and soft fruits, e.g. *P. leucotricha* on apples; *Polymyxa* spp., e.g. on cereals, such as barley and wheat (*P. graminis*) and sugar beets (*P. betae*) and thereby transmitted viral diseases; *Pseuodocercosporella herpotrichoides* (eyespot, teleomorph: *Tapesia yallundae*) on cereals, e.g. wheat or barley; *Pseudoperonospora* (downy mildew) on various plants, e.g. *P. cubensis* on cucurbits or *P. humili* on hop; *Pseudopezicula tracheiphila* (red fire disease or 'rotbrenner', anamorph: *Phialophora*) on vines; *Puccinia* spp. (rusts) on various plants, e.g. *P. triticina* (brown or leaf rust), *P. striiformis* (stripe or yellow rust), *P. hordei* (dwarf rust), *P. graminis* (stem or black rust) or *P. recondita* (brown or leaf rust) on cereals, such as e.g. wheat, barley or rye, and asparagus (e.g. *P. asparagi*); *Pyrenophora* (anamorph: *Drechslera*) *tritici-repentis* (tan spot) on wheat or *P. teres* (net blotch) on barley; *Pyricularia* spp., e.g. *P. oryzae* (teleomorph: *Magnaporthe grisea*, rice blast) on rice and *P. grisea* on turf and cereals; *Pythium* spp. (damping-off) on turf, rice, corn, wheat, cotton, rape, sunflowers, soybeans, sugar beets, vegetables and various other plants (e.g. *P. ultimum* or *P. aphanidermatum*); *Ramularia* spp., e.g. *R. collocygni* (Ramularia leaf spots, Physiological leaf spots) on barley and *R. beticola* on sugar beets; *Rhizoctonia* spp. on cotton, rice, potatoes, turf, corn, rape, potatoes, sugar beets, vegetables and various other plants, e.g. *R. solani* (root and stem rot) on soybeans, *R. solani* (sheath blight) on rice or *R. cerealis* (Rhizoctonia spring blight) on wheat or barley; *Rhizopus stolonifer* (black mold, soft rot) on strawberries, carrots, cabbage, vines and tomatoes; *Rhynchosporium secalis* (scald) on barley, rye and triticale; *Sarocladium oryzae* and *S. attenuatum* (sheath rot) on rice; *Sclerotinia* spp. (stem rot or white mold) on vegetables and field crops, such as rape, sunflowers (e.g. *S. sclerotiorum*) and soybeans (e.g. *S. rolfsi* or *S. sclerotiorum*); *Septoria* spp. on various plants, e.g. *S. glycines* (brown spot) on soybeans, *S. tritici*(Septoria blotch) on wheat and *S.* (syn. *Stagonospora*) *nodorum* (Stagonospora blotch) on cereals; *Uncinula* (syn. *Erysiphe*) *necator*(powdery mildew, anamorph: *Oidium tuckeri*) on vines; *Setospaeria* spp. (leaf blight) on corn (e.g. *S. turcicum*, syn. *Helminthosporium turcicum*) and turf; *Sphacelotheca* spp. (smut) on corn, (e.g. *S. reiliana*: head smut), sorghum and sugar cane; *Sphaerotheca fuliginea* (powdery mildew) on cucurbits; *Spongospora subterranea* (powdery scab) on potatoes and thereby transmitted viral diseases; *Stagonospora* spp. on cereals, e.g. *S. nodorum* (Stagonospora blotch, teleomorph: *Leptosphaeria* [syn. *Phaeosphaeria*] *nodorum*) on wheat; *Synchytrium endobioticum* on potatoes (potato wart disease); *Taphrina* spp., e.g. *T. deformans* (leaf curl disease) on peaches and *T. pruni* (plum pocket) on plums; *Thielavibpsis* spp. (black root rot) on tobacco, pome fruits, vegetables, soybeans and cotton, a g. *T. basicola* (syn. *Chalara elegans*); *Tilletia* spp. (common bunt or stinking smut) on cereals, such as e.g. *T. tritici* (syn. *T. caries*, wheat bunt) and *T. controversa* (dwarf bunt) on wheat; *Typhula incarnata* (grey snow mold) on barley or wheat; *Urocystis* spp., e.g. *U. occulta* (stem smut) on rye; *Uromyces* spp. (rust) on vegetables, such as beans (e.g. *U. appendiculatus*, syn. *U. phaseoli*) and sugar beets (e.g. betae); *Ustilago* spp. (loose smut) on cereals (e.g. *U. nuda* and *U. avaenae*), corn (e.g. *U. maydis*: corn smut) and sugar cane; *Venturia* spp. (scab) on apples (e.g. *V. inaequalis*) and pears; and *Verticillium* spp. (wilt) on various plants, such as fruits and ornamentals, vines, soft fruits, vegetables and field crops, e.g. *V. dahliae* on strawberries, rape, potatoes and tomatoes.

The inventive mixtures are also suitable for controlling fungal diseases occurring in the protection of materials. The term "protection of materials" is to be understood to denote the protection of technical and non-living materials, such as adhesives, glues, wood, paper and paperboard, textiles, leather, paint dispersions, plastics, coiling lubricants, fiber or fabrics, against the infestation and destruction by harmful microorganisms, such as fungi and bacteria. As to the protection of wood and other materials, the particular attention is paid to the following harmful fungi: Ascomycetes such as *Ophiostoma* spp., *Ceratocystis* spp., *Aureobasidium pullulans*, *Sclerophoma* spp., *Chaetomium* spp., *Humicola* spp., *Petriella* spp., *Trichurus* spp.; Basidiomycetes such as *Coniophora* spp., *Coriolus* spp., *Gloeophyllum* spp., *Lentinus* spp., *Pleurotus* spp., *Poria* spp., *Serpula* spp. and *Tyromyces* spp., Deuteromycetes such as *Aspergillus* spp., *Cladosporium* spp., *Penicillium* spp., *Trichorma* spp., *Alternaria* spp., *Paecilomyces* spp. and Zygomycetes such as *Mucor* spp., and in addition in the protection of stored products the following yeast fungi are worthy of note: *Candida* spp. and *Saccharomyces cerevisae*.

They are particularly important for controlling a multitude of harmful fungi and aminal pests on various cultivated plants, such as cereals, e.g. wheat, rye, barley, triticale, oats or rice; beet, e.g. sugar beet or fodder beet; fruits, such as pomes, stone fruits or soft fruits, e.g. apples, pears, plums, peaches, almonds, cherries, strawberries, raspberries, blackberries or gooseberries; leguminous plants, such as lentils, peas, alfalfa or soybeans; oil plants, such as rape, mustard, olives, sunflowers, coconut, cocoa beans, castor oil plants, oil palms, ground nuts or soybeans; cucurbits, such as squashes, cucumber or melons; fiber plants, such as cotton, flax, hemp or jute; citrus fruit, such as oranges, lemons, grapefruits or mandarins; vegetables, such as spinach, lettuce, asparagus, cabbages, carrots, onions, tomatoes, potatoes, cucurbits or paprika; lauraceous plants, such as avocados, cinnamon or camphor; energy and raw material plants, such as corn, soybean, rape, sugar cane or oil palm; corn; tobacco; nuts; coffee; tea; bananas; vines (table grapes and grape juice grape vines); hop; turf; sweet leaf (also called Stevia); natural rubber plants or ornamental and forestry plants, such as flowers, shrubs, broad-leaved trees or evergreens, e.g. conifers; and on the plant propagation material, such as seeds, and the crop material of these plants. Preferably, the inventive mixtures of the present invention are used for controlling a multitude of fungi on field crops, such as potatoes sugar beets, tobacco, wheat, rye, barley, oats, rice, corn, cotton, soybeans, rape, legumes, sunflowers, coffee or sugar cane; fruits; vines; ornamentals; or vegetables, such as cucumbers, tomatoes, beans or squashes.

Preferably, the treatment of plant propagation materials with the inventive mixtures is used for controlling a multitude of fungi on cereals, such as wheat, rye, barley and oats; rice, corn, cotton and soybeans.

The inventive mixtures exhibit also outstanding action against animal pests from the following orders:

insects from the order of the lepidopterans (Lepidoptera), for example *Agrotis ypsilon, Agrotis segetum, Alabama argillacea, Anticarsia gemmatalis, Argyresthia conjugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea giandiosella, Earias insulana, Elasmopalpus lignosellus, Eupoecilia ambiguella, Evetria bouliana, subterranea, Galleria mellonella, Grapholitha funebrana, Grapholitha molesta, Heliothis armigera, Heliothis virescens, Heliothis zea, Hellula undalis, Hibernia defoliaria, Hyphantria cunea, Hyponomeuta malinellus, Keiferia lycopersicella, Lambdina fiscellaria, Laphygma exigua, Leucoptera coffeella, Leucoptera scitella, Lithocollegs blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flammea, Pectinophora gossypiella, Peridroma saucia, Phalera bucephala, Phthorimaea operculella, Phyllocnistis citrella, Pieris brassicae, Plathypena scabra, Pluralla xylostella, Pseudoplusia includens, Rhyacionia frustrana, Scrobipalpula absoluta, Sitotroga cerealella, Sparganothis pilleriana, Spodoptera frugiperda, Spodoptera littoralis, Spodoptera litura, Thaumatopoea pityocampa, Tortrix viridana, Trichoplusia ni* and *Zeiraphera canadensis* beetles (Coleoptera), for example *Agrilus sinuatus, Agriotes lineatus, Agriotes obscurus, Amphimallus solstitialis, Anisandrus dispar, Anthonomus grandis, Anthonomus pomorum, Aphthona euphoridae, Athous haemorrhoidalis, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Cetonia aurata, Ceuthorrhynchus assimilis, Ceuthorrhynchus napi, Chaetocnema tibialis, Conoderus vespertinus, Crioceris asparagi, Ctenicera ssp., Diabrotica longicornis, Diabrotica semipunctate, Diabrotica 12 punctata Diabrotica speciosa, Diabrotica virgifera, Epilachna varivestis, Epitrix hirtipennis, Eutinobothrus brasiliensis, Hylobius abietis, Hypera brunneipennis, Hypera postica, Ips typographus, Lema bilineata, Lema melanopus, Leptinotarsa decemlineata, Limonius californicus, Lissorhoptrus oryzophllus, Melanotus communis, Meligethes aeneus, Melolontha hippocastani, Melolontha melolontha, Oulema oryzae, Ortiorrhynchus sulcatus, Otiorrhynchus ovatus, Phaedon cochleariae, Phyllobius pyri, Phyllotreta chrysocephala, Phyllophaga* sp., *Phyllopertha horticola, Phyllotreta nemorum, Phyllotreta striolata, Popillia japonica, Sitona lineatus* and *Sitophilus granaria* flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Ceratigs capitata, Chrysomya bezziana, Chrysomya hominivorax, Chrysomya macellaria, Chrysops discalis, Chrysops silacea, Chrysops atlanticus, Cochliomyia hominivorax, Contarinia sorghicola Cordylobia anthropophaga, Culicoides furens, Culex pipiens, Culex nigripalpus, Culex quinquefasciatus, Culex tarsalis, Culiseta inornata, Culiseta melanura, Dacus cucurbitae, Dacus oleae, Dasineura brassicae, Delia antique, Delia coarctata, Delia platura, Delia radicum, Dermatobia hominis, Fannia canicularis, Geomyza Tripunctata, Gasterophilus intestinalis, Glossina morsitans, Glossina palpalis, Glossina fuscipes, Glossina tachinoides, Haematobia irritans, Haplodiplosis equestris, Hippelates* spp., *Hylemyia platura, Hypoderma lineata, Leptoconops torrens, Lirlomyza sativae, Liriomyza trifolii, Lucilia caprina, Lucilia cuprina, Lucilia sericata, Lycoria pectoralis, Mansonia titillanus, Mayetiola destructor, Musca domestica, Muscina stabulans, Oestrus ovis, Opomyza forum, Oscinella frit, Pegomya hysocyami, Phorbia antiqua, Phorbia brassicae, Phorbia coarctata, Phlebotomus argentipes, Psorophora columblae, Psila rosae, Psorophora discolor, Prosimulium mixtum, Rhagoletis cerasi, Rhagoletis pomonella, Sarcophaga haemorrhoidalis, Sarcophaga* sp., *Simulium vittatum, Stomoxys calcitrans, Tabanus bovinus, Tabanus atratus, Tabanus lineola,* and *Tabanus similis, Tipula oleracea,* and *Tipula paludosa* thrips (Thysanoptera), e.g. *Dichromothrips corbetti, Dichromothrips* ssp, *Frankliniella fusca, Frankliniella occidentalis, Frankliniella tritici, Scirtothrips citri, Thrips oryzae, Thrips palmi* and *Thrips tabaci* termites (Isoptera), e.g. *Calotermes flavicollis, Leucotermes flavipes, Heterotermes aureus, Reticulitermes fiavipes, Reticulitermes virginicus, Reticulitermes lucifugus, Termes natalensis,* and *Coptotermes formosanus* cockroaches (Blattaria—Blattodea), e.g. *Blattella germanica, Blattella asahinae, Periplaneta americana, Periplaneta japonica, Periplaneta brunnea, Periplaneta fuliginosa, Periplaneta australasiae,* and *Blatta orientalis* true bugs (Hemiptera), e.g. *Acrosternum hilare, Blissus leucopterus, Cyrtopeltis notatus, Dysdercus cingulatus, Dysdercus intermedius, Eurygaster integriceps, Euschistus impictiventris, Leptoglossus phyllopus, Lygus lineolaris, Lygus pratensis, Nezara viridula, Piesma quadrata, Solubea insularis, Thyanta perditor, Acyrthosiphon onobrychis, Adelges laricis, Aphidula nasturtii, Aphis fabae, Aphis forbesi, Aphis pomi, Aphis gossypii, Aphis grossulariae, Aphis schneideri, Aphis spiraecola, Aphis sambuci, Acyrthosiphon pisum, Aulacorthum solani, Bemisia argentifolii, Brachycaudus cardui, Brachycaudus helichrysi, Brachycaudus persicae,*

*Brachycaudus prunicola, Brevicoryne brassicae, Capitophorus horni, Cerosipha gossypii, Chaetosiphon fragaefolii, Cryptomyzus ribis, Dreyfusia nordmannianae, Dreyfusia piceae, Dysaphis radicola, Dysaulacorthum pseudosolani, Dysaphis plantaginea, Dysaphis pyri, Empoasca fabae, Hyalopterus pruni, Hyperomyzus lactucae, Macrosiphum avenae, Macrosiphum euphorbiae, Macrosiphon rosae, Megoura viviae, Melanaphis pyrarius, Metopolophium dirhodum, Myzus persicae, Myzus ascalonicus, Myzus cerasi, Myzus varians, Nasonovia ribis-nigri, Nilaparvata lugens, Pemphigus bursarius, Perkinsiella saccharicida, Phorodon humuli, Psylla mali, Psylla piri, Rhopalomyzus ascalonicus, Rhopalosiphum maidis, Rhopalosiphum padi, Rhopalosiphum insertum, Sappaphis mala, Sappaphis mali, Schizaphis graminum, Schizoneura lanuginosa, Sitobion avenae, Trialeurodes vaporariorum, Toxoptera aurantii* and, *Viteus vitifolii, Cimex lectularius, Cimex hemipterus, Reduvius senilis, Triatoma* spp., and *Arilus ctitatus*.

ants, bees, wasps, sawflies (Hymenoptera), e.g. *Athalia rosae, Atta cephalotes, Atta capiguara, Atta cephalotes, Atta laevigata, Atta robusta, Alta sexdens, Alta texana, Crematogaster* spp., *Hoplocampa minuta, Hoplocampa testudinea, Monomorium pharaonis, Solenopsis geminata, Solenopsis invicta, Solenopsis richteri, Solenopsis xyloni, Pogonomyrmex barbatus, Pogonomyrmex californicus, Pheidole megacephala, Dasymutfila occidentalis, Bombus* spp. *Vespula squamosa, Paravespula vulgaris, Paravespula pennsylvanica, Paravespula germanica, Dolichovespula maculata, Vespa crabro, Polistes rubiginosa, Camponotus floridanus,* and *Linepithema humile* crickets, grasshoppers, locusts (Orthoptera), e.g. *Acheta domestica, Gryllotalpa gryllotalpa, Locusta migratoria, Melanoplus bivittatus, Melanoplus femurrubrum, Melanoplus mexicanus, Melanoplus sanguinipes, Melanoplus spretus, Nomadacris septemfasciata, Schistocerca americana, Schistocerca gregaria, Dociostaurus maroccanus, Tachycines asynamorus, Oedaleus senegalensis, Zonozerus variegatus, Hieroglyphus daganensis, Kraussaria angulifera, Calliptamus italicus, Chortoicetes terminifera,* and *Locustana pardalina*

Arachnoidea, such as arachnids (Acarina), e.g. of the families Argasidae, Ixodidae and Sarcoptidae, such as *Amblyomma americanum, Amblyomma variegatum, Ambryomma maculatum, Argas persicus, Boophilus annulatus, Boophilus decoloratus, Boophilus microplus, Dermacentor silvarum, Dermacentor andersoni, Dermacentor variabilis, Hyalomma truncatum, Ixodes ricinus, Ixodes rubicundus, Ixodes scapularis, Ixodes holocyclus, Ixodes pacificus, Ornithodorus moubata, Ornithodorus hermsi, Ornithodorus turicata, Ornithonyssus bacoti, Otobius megnini, Dermanyssus gallinae, Psoroptes ovis, Rhipicephalus sanguineus, Rhipicephalus appendiculatus, Rhipicephalus evertsi, Sarcoptes scabiei,* and *Eriophyidae* spp. such as *Aculus schlechtendali, Phyllocoptrata oleivora* and *Eriophyes sheldoni*, Tarsonemidae spp. such as *Phytonemus pallidus* and *Polyphagotarsonemus latus*, Tenuipalpidae spp. such as *Brevialpus phoenicis*, Tetranychidae spp. such as *Tetranychus cinnabarinus, Tetranychus kanzawai, Tetranychus pacificus, Tetranychus tetanus* and *Tetranychus urticae, Panonychus ulmi, Panonychus citri,* and *Oligonychus pratensis*; Araneida, e.g. *Latrodectus mactans,* and *Loxosceles reclusa* fleas (Siphonaptera), e.g. *Ctenocephalides felis, Ctenocephalides canis, Xenopsylla cheopis, Pulex irritans, Tunga penetrans,* and *Nosopsyllus fasciatus* silverfish, firebrat (Thysanura), e.g. *Lepisma saccharin* and *Thermobia domestica* centipedes (Chilopoda), e.g. *Scutigera coleoptrata* millipedes (Diplopoda), e.g. *Narceus* spp.

Earwigs (Dermaptera), e.g. *forficula auricularia* lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus* and *Solenopotes capillatus* plant parasitic nematodes such as root-knot nematodes, *Meloidogyne arenaria, Meloidogyne chitwoodi, Meloidogyne exigua, Meloidogyne hapla, Meloidogyne incognita, Meloidogyne javanica* and other *Meloidogyne* species; cyst nematodes, *Globodera rostochiensis, Globodera pallida, Globodera tabacum* and other *Globodera* species, *Heterodera avenae, Heterodera glycines, Heterodera schachtii, Heterodera trifolli,* and other *Heterodera* species; seed gall nematodes, *Anguina funesta, Anguina tritici* and other *Anguina* species; stem and foliar nematodes, *Aphelenchoides besseyi, Aphelenchoides fragariae, Aphelenchoides ritzemabosi* and other *Aphelenchoides* species; sting nematodes, *Belonolaimus longicaudatus* and other *Belonolaimus* species; pine nematodes, *Bursaphelenchus xylophilus* and other *Bursaphelenchus* species; ring nematodes, *Criconema* species, *Criconemella* species, *Criconemoides* species, and *Mesocriconema* species; stem and bulb nematodes, *Ditylenchus destructor, Ditylenchus dipsaci, Ditylenchus myceliophagus* and other *Ditylenchus* species; awl nematodes, *Dolichodorus* species; spiral nematodes, *Helicotylenchus dihystera, Helicotylenchus multicinctus* and other *Helicotylenchus* species, *Rotylenchus robustus* and other *Rotylenchus* species; sheath nematodes, *Hemicycliophora* species and *Hemicriconemoides* species, *Hirshmanniella* species; lance nematodes, *Hoplolaimus columbus, Hoplolaimus galeatus* and other *Hoplolaimus* species; false root-knot nematodes, *Nacobbus aberrans* and other *Nacobbus* species; needle nematodes, *Longidorus elongates* and other *Longidorus* species; pin nematodes, *Paratylenchus* species; lesion nematodes, *Pratylenchus brachyurus, Pratylenchus coffeae, Pratylenchus curvitatus, Pratylenchus goodeyi, Pratylencus neglectus, Pratylenchus penetrans, Pratylenchus scnbneri, Pratylenchus vulnus, Pratylenchus zeae* and other *Pratylenchus* species; *Radinaphelenchus cocophilus* and other *Radinaphelenchus* species, burrowing nematodes, *Radopholus simills* and other *Radopholus* species; reniform nematodes, *Rotylenchulus reniformis* and other *Rotylenchulus* species; *Scutellonema* species; stubby root nematodes, *Trichodorus primitivus* and other *Trichodorus* species; *Paratrichodorus minor* and other *Paratrichodorus* species; stunt nematodes, *Tylenchorhynchus claytoni, Tylenchorhynchus dubius* and other *Tylenchorhynchus* species and *Merlinius* species; citrus nematodes, *Tylenchulus semipenetrans* and other *Tylenchulus* species; dagger nematodes, *Xiphinema americanum, Xiphinema index, Xiphinema diversicaudatum* and other *Xiphinema* species; and other plant parasitic nematode species.

The mixtures according to the invention can be applied to any and all developmental stages of pests, such as egg, larva, pupa, and adult. The pests may be controlled by contacting the target pest, its food supply, habitat, breeding ground or its locus with a pesticidally effective amount of the inventive mixtures or of compositions comprising the mixtures.

"Locus" means a plant, plant propagation material (preferably seed), soil, area, material or environment in which a pest is growing or may grow.

In general, "pesticidally effective amount" means the amount of the inventive mixtures or of compositions comprising the mixtures needed to achieve an observable effect on growth, including the effects of necrosis, death, retardation, prevention, and removal, destruction, or otherwise diminishing the occurrence and activity of the target organism. The pesticidally effective amount can vary for the various mixtures/compositions used in the invention. A pesticidally effective amount of the mixtures/compositions will also vary according to the prevailing conditions such as desired pesticidal effect and duration, weather, target species, locus, mode of application, and the like.

As said above, the present invention comprises a method for improving the health of plants, wherein the plant, the locus where the plant is growing or is expected to grow or plant propagation material, from which the plant grows, is treated with an plant health effective amount of an inventive mixture.

The term "plant health effective amount" denotes an amount of the inventive mixtures, which is sufficient for achieving plant health effects as defined hereinbelow. More exemplary information about amounts, ways of application and suitable ratios to be used is given below. Anyway, the skilled artisan is well aware of the fact that such an amount can vary in a broad range and is dependent on various factors, e.g. the treated cultivated plant or material and the climatic conditions.

The term "effective amount" comprises the terms "plant health effective amount" and/or "pesticidally effective amount" as the case may be.

When preparing the mixtures, it is preferred to employ the pure active compounds, to which further active compounds against pests, such as insecticides, herbidices, fungicides or else herbicidal or growth-regulating active compounds or fertilizers can be added as further active components according to need.

The inventive mixtures are employed by treating the fungi or the plants, plant propagation materials (preferably seeds), materials or soil to be protected from fungal attack with a pesticidally effective amount of the active compounds. The application can be carried out both before and after the infection of the materials, plants or plant propagation materials (preferably seeds) by the pests.

Preferably, the inventive mixtures are employed by treating the fungi or the plants or soil to be protected from pesticidal attack via foliar application with a pesticidally effective amount of the active compounds. Also herein, the application can be carried out both before and after the infection of the plants by the pests.

In the method of combating harmful fungi depending on the type of compound and the desired effect, the application rates of the mixtures according to the invention are from 0.1 g/ha to 10000 g/ha, preferably 2 g/ha to 2500 g/ha, more preferably from 5 to 1000 g/ha, most preferably from 10 to 750 g/ha, in particular from 20 to 500 g/ha.

In the method of combating animal pests (insects, acarids or nematodes) depending on the type of compound and the desired effect, the application rates of the mixtures according to the invention are from 0.1 g/ha to 10000 g/ha, preferably 1 g/ha to 5000 g/ha, more preferably from 20 to 1000 g/ha, most preferably from 10 to 750 g/ha, in particular from 20 to 500 g/ha.

The inventive mixtures or compositions of these mixtures can also be employed for protecting plants from attack or infestation by animal pests (insects, acarids or nematodes) comprising contacting a plant, or soil or water in which the plant is growing.

In the context of the present invention, the term plant refers to an entire plant, a part of the plant or the propagation material of the plant.

Plants and as well as the propagation material of said plants, which can be treated with the inventive mixtures include all genetically modified plants or transgenic plants, e.g. crops which tolerate the action of herbicides or fungicides or insecticides owing to breeding, including genetic engineering methods, or plants which have modified characteristics in comparison with existing plants, which can be generated for example by traditional breeding methods and/or the generation of mutants, or by recombinant procedures.

For example, mixtures according to the present invention can be applied (as seed treatment, spray treatment, in furrow or by any other means) also to plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-transtional modification of protein(s), oligo- or polypeptides e.g. by glycosylation or polymer additions such as prenylated, acetylated or farnesylated moieties or PEG moieties.

Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559,024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringi-*

*ensis*, such as δ-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insectcidal proteins of bacteria colonizing nematodes, e.g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins.

Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the CrylAc toxin), Bollgard® I (cotton cultivars producing the CrylAc toxin), Bollgard® II (cotton cultivars producing CrylAc and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the CrylAc toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the mexican wild potato *Solanum bulbocastanum*) or T4-lysozym (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

In a further embodiment of the invention, the inventive mixtures are used for the protection of the seed and the seedlings' roots and shoots, preferably the seeds.

Seed treatment can be made into the seedbox before planting into the field.

For seed treatment purposes, the weight ration in the mixtures of the present invention generally depends from the properties of the compounds of the inventive mixtures.

Compositions, which are especially useful for seed treatment are e.g.:

A Soluble concentrates (SL, LS)
D Emulsions (EW, EO, ES)
E Suspensions (SC, OD, FS)
F Water-dispersible granules and water-soluble granules (WG, SG)
G Water-dispersible powders and water-soluble powders (WP, SP, WS)
H Gel-Formulations (GF)
I Dustable powders (DP, DS)

These compositions can be applied to plant propagation materials, particularly seeds, diluted or undiluted. These compositions can be applied to plant propagation materials, particularly seeds, diluted or undiluted. The compositions in question give, after two-to-tenfold dilution, active substance concentrations of from 0.01 to 60% by weight, preferably from 0.1 to 40% by weight, in the ready-to-use preparations. Application can be carried out before or during sowing. Methods for applying or treating agrochemical compounds and compositions thereof, respectively, on to plant propagation material, especially seeds, are known in the art, and include dressing, coating, pelleting, dusting and soaking application methods of the propagation material (and also in furrow treatment). In a preferred embodiment, the compounds or the compositions thereof, respectively, are applied on to the plant propagation material by a method such that germination is not induced, e.g. by seed dressing, pelleting, coating and dusting.

In the treatment of plant propagation material (preferably seed), the application rates of the inventive mixture are generally for the formulated product (which usually comprises from 10 to 750 g/l of the active(s)).

The invention also relates to the propagation products of plants, and especially the seed comprising, that is, coated with and/or containing, a mixture as defined above or a composition containing the mixture of two or more active ingredients or a mixture of two or more compositions each providing one of the active ingredients. The plant propagation material (preferably seed) comprises the inventive mixtures in an amount of from 0.1 g to 10 kg per 100 kg of plant propagation material (preferably seed), preferably 0.1 g to 1 kg per 100 kg of plant propagation material (preferably seed).

For example, the ratio by weight for compound II is herein preferably between 0.5-200 g/100 kg plant propagation material (preferably seed), more preferred 1 to 50 g/100 kg plant propagation material (preferably seed) and most preferred 1 to 20 g/100 kg plant propagation material (preferably seed).

For example, the ratio by weight of compound I is herein preferably between 1-2000 g/100 kg plant propagation material (preferably seed), more preferred 10 to 1000 g/100 kg plant propagation material (preferably seed), most preferred 25 to 750 g/100 kg plant propagation material (preferably seed) and utmost preferred 50-500 g/100 kg plant propagation material (preferably seed).

The separate or joint application of the compounds of the inventive mixtures is carried out by spraying or dusting the seeds, the seedlings, the plants or the soils before or after sowing of the plants or before or after emergence of the plants.

The inventive mixtures are effective through both contact (via soil, glass, wall, bed net, carpet, plant parts or animal parts), and ingestion (bait, or plant part) and through trophallaxis and transfer.

Preferred application methods are into water bodies, via soil, cracks and crevices, pastures, manure piles, sewers, into water, on floor, wall, or by perimeter spray application and bait.

According to another preferred embodiment of the invention, for use against non phytophathogenic pests such as ants, termites, wasps, flies, mosquitoes, crickets, locusts, or cockroaches the inventive mixtures are prepared into a bait preparation.

The bait can be a liquid, a solid or a semisolid preparation (e.g. a gel). The bait employed in the composition is a product which is sufficiently attractive to incite insects such as ants, termites, wasps, flies, mosquitoes, crickets etc. or cockroaches to eat it. This attractant may be chosen from feeding stimulants or para and/or sex pheromones readily known in the art.

Methods to control infectious diseases transmitted by non-phytophathogenic insects (e.g. malaria, dengue and yellow fever, lymphatic filariasis, and leishmaniasis) with the inventive mixtures and their respective compositions also comprise treating surfaces of huts and houses, air spraying and impregnation of curtains, tents, clothing items, bed nets, tsetse-fly trap or the like. Insecticidal compositions for application to fibers, fabric, knitgoods, non-wovens, netting material or foils and tarpaulins preferably comprise a composition including the inventive mixtures, optionally a repellent and at least one binder.

The inventive mixtures and the compositions comprising them can be used for protecting wooden materials such as trees, board fences, sleepers, etc. and buildings such as houses, outhouses, factories, but also construction materials, furniture, leathers, fibers, vinyl articles, electric wires and cables etc. from ants and/or termites, and for controlling ants and termites from doing harm to crops or human being (e.g. when the pests invade into houses and public facilities).

In the case of soil treatment or of application to the pests dwelling place or nest, the quantity of active ingredient ranges from 0.0001 to 500 g per 100 $m^2$, preferably from 0.001 to 20 g per 100 $m^2$.

Customary application rates in the protection of materials are, for example, from 0.01 g to 1000 g of active compound per $m^2$ treated material, desirably from 0.1 g to 50 g per $m^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

For use in bait compositions, the typical content of active ingredient is from 0.0001 weight % to 15 weight %, desirably from 0.001 weight % to 5% weight % of active compound. The composition used may also comprise other additives such as a solvent of the active material, a flavoring agent, a preserving agent, a dye or a bitter agent. Its attractiveness may also be enhanced by a special color, shape or texture.

For use in spray compositions, the content of the mixture of the active ingredients is from 0.001 to 80 weights %, preferably from 0.01 to 50 weight % and most preferably from 0.01 to 15 weight %.

The invention is further illustrated by, but not limited to the following examples.

EXAMPLES

The active compounds were formulated separately as a stock solution having a concentration of 10000 ppm in dimethyl sulfoxide.

Activity against rice blast *Pyricularia oryzae* in the microtiterplate test (Pyrior)

The stock solutions were mixed according to the ratio, pipetted onto a micro titer plate (MTP) and diluted with water to the stated concentrations. A spore suspension of *Pyricularia oryzae* in an aqueous biomalt solution was then added. The plates were placed in a water vapor-saturated chamber at a temperature of 18° C. Using an absorption photometer, the MTPs were measured at 405 nm 7 days after the inoculation. The measured parameters were compared to the growth of the active compound-free control variant (100%) and the fungus-free and active compound-free blank value to determine the relative growth in % of the pathogens in the respective active compounds. These percentages were converted into efficacies.

The expected efficacies of active compound mixtures were determined using Colby's formula [R. S. Colby, "Calculating synergistic and antagonistic responses of herbicide combinations", Weeds 15, 20-22 (1967)] and compared with the observed efficacies.

| Active compound/ active mixture | Concentration (ppm) | Mixture | Observed efficacy | Calculated efficacy according to Colby (%) | Synergism (%) |
|---|---|---|---|---|---|
| Pyraclostrobin | 0.004 | — | 23 | | |
| alpha-Cypermethrin | 1 | — | 1 | | |

-continued

| Active compound/ active mixture | Concentration (ppm) | Mixture | Observed efficacy | Calculated efficacy according to Colby (%) | Synergism (%) |
|---|---|---|---|---|---|
| Pyraclostrobin alpha-Cypermethrin | 0.004 1 | 1:250 | 67 | 25 | 42 |

The invention claimed is:

1. Mixtures comprising, as active components,
   1) of bifenthrin; and
   2) pyraclostrobin;
      in synergistic effective amounts, wherein the ratio by weight of bifenthrin and pyraclostrobin is from 1:16 to 16:1.

2. A pesticidal composition, comprising a liquid or solid carrier and a mixture as defined in claim 1.

3. A method for controlling pests selected from the group consisting of *Botrytis cinerea, Alternaria alternate*, and *Pyricularia oryzae*, wherein (a) the pest, their habitat, breeding grounds, their locus or the plants to be protected against pest attack, the soil or plant propagation material; or (b) the plant, the locus where the plant is growing or is expected to grow or plant propagation material from which the plant grows;

are treated with an effective amount of a mixture as defined in claim 1.

4. A method for protection of plant propagation material from pests selected from the group consisting of *Botrytis cinerea, Alternaria alternate*, and *Pyricularia oryzae*, comprising contacting the plant propagation materials with a mixture as defined in claim 1 in pesticidally effective amounts.

5. A method as claimed in claim 4, wherein the mixture as defined in claim 1 is applied in an amount of from 0.01 g to 10 kg per 100 kg of plant propagation materials.

6. A method as claimed in claim 3, wherein the compounds as defined in claim 1 are applied simultaneously, that is jointly or separately, or in succession.

7. Plant propagation material, comprising the mixture as defined in claim 1 in an amount of from 0.01 g to 10 kg per 100 kg of plant propagation materials.

* * * * *